United States Patent [19]

Binns et al.

[11] Patent Number: 5,631,343
[45] Date of Patent: May 20, 1997

[54] ENZYMATIC SYNTHESIS

[75] Inventors: Falmai Binns; Alan Taylor, both of Accrington, United Kingdom

[73] Assignee: Baxenden Chemicals Limited, United Kingdom

[21] Appl. No.: 446,711

[22] PCT Filed: Nov. 30, 1993

[86] PCT No.: PCT/GB93/02461

§ 371 Date: Jun. 15, 1995

§ 102(e) Date: Jun. 15, 1995

[87] PCT Pub. No.: WO94/12652

PCT Pub. Date: Jun. 9, 1994

[30] Foreign Application Priority Data

Nov. 30, 1992 [GB] United Kingdom ............. 9225054

[51] Int. Cl.$^6$ ................. C08G 63/82; C12P 17/00
[52] U.S. Cl. ............ 528/274; 528/272; 528/301; 528/361; 525/440; 264/239; 435/117; 435/132; 435/135; 435/931
[58] Field of Search ................... 528/272, 274, 528/301, 361; 525/440; 264/239; 435/117, 132, 135, 531

[56] References Cited

PUBLICATIONS

Gross et al "Enzymes In Organic Media as Catalysts for Polyester Synthesis", Polym. Mater. Sci. Eng., 74 (2–3), p. 67 (1996), Aug. 16, 1996.

*Primary Examiner*—Samuel A. Acquah
*Attorney, Agent, or Firm*—Nixon & Vanderhye

[57] ABSTRACT

A process for producing a polyester comprising as repeating units (i) residues of at least one aliphatic hydroxycarboxylic acid, aminocarboxylic acid, or derivative thereof; or (ii) residues of (a) at least one aliphatic dicarboxylic acid or derivative thereof, (b) at least one aliphatic hydroxyamine, diol, polyol, diamine or polyamine, and optionally (c) at least one aliphatic hydroxycarboxylic acid, aminocarboxylic acid or derivative thereof;

comprises reacting the components defined in (i) or components defined in (ii) in the absence of a solvent and in the presence of a lipase.

22 Claims, No Drawings

ENZYMATIC SYNTHESIS

This application is 371 of PCT/GB93/02461 filed Nov. 30, 1993.

The present invention relates to a process for producing polyesters or polyester(amide)s by enzyme catalysed reaction of monomers and to polyesters or polyester(amide)s having unique properties which may be obtained by that process.

Polyesters are well known industrial products finding applications principally as moulded articles in, for instance, the car industry. They are also of interest as the intermediates in the production of polyurethanes, which are also used to form moulded articles. Polyesters are reacted with isocyanates to form polyurethanes. The characteristics of the resulting polyurethane depend at least in part on those of the polyester.

Polyesters are typically produced by chemically catalysed reactions using elevated temperatures, strong acids and long reaction times. Competition between esterification, transesterification and hydrolysis limits the molecular weight of the products. Moreover these processes are accompanied by the formation of quantities of unwanted by-products, such as cyclic esters, and have the added disadvantage that the catalyst is difficult to remove. Furthermore, it is necessary to remove the water produced by the reaction in order to force the equilibrium towards products. If the presence of by-products and residual catalyst is not to degrade the properties of the desired material, complex arrangements are required to prevent their formation or remove them after the main reaction (see e.g. EP-A-0425201).

Polyester(amide)s were fashionable as materials for moulded products in the 1960's and 1970's but became less popular because they were found to become yellow as they aged. There has recently been an increased demand for polyester(amide)s especially those based on adipic acid/methylethanolamine. However, methylethanolamine has a relatively low boiling point and cannot be used in conventional chemically catalysed, high temperature polyesterifications unless the reaction is conducted under very high pressure.

The present invention seeks to overcome the difficulties of chemically catalysed reactions by use of lipase enzymes. Whilst lipasos have been known for some time for simple esterification and transesterification reactions (see, e.g. EP-A-0383 405) and stereoselective oligomerisations (see, e.g. Margolin A. L. et al., *Tet. Letters*, 28: 1607–1610,(1987)), only limited use has been made of lipasos in polyesterification. In particular Wallace and Morrow, *J. Polymer Science Part A*, 27, 2553–2562 (1989) and Gutman, *Mat. Res. Soc. Symp. Proc.*, 174, 217–222 (1990) have succeeded in forming polyesters of high weight average molecular weight starting from dicarboxylic acid diestars where the ester moiety is highly activated (2,2,2-trichloroethyl esters) or from esters of hydroxycarboxylic acids and diesters of hydroxy dicarboxylic acids. However these processes have relied upon the use of organic solvents.

The present invention relates to a solventless enzymatic polyesterification process which not only avoids the disadvantages of earlier chemical and enzymatic techniques but remarkably affords polyesters of high weight average molecular weight, and narrow dispersity whilst also being extremely pure in terms of freedom from unwanted by-products. The invention further provides novel polyesters obtainable by this process.

The present invention in one aspect provides a process for producing a polyester comprising as repeating units (i) residues of at least one aliphatic hydroxycarboxylic acid or derivative thereof; or (ii) residues of (a) at least one aliphatic dicarboxylic acid or derivative thereof, (b) at least one aliphatic hydroxyamine, diol or polyol, and optionally (c) at least one aliphatic hydroxycarboxylic acid or derivative thereof;

which process comprises reacting the components defined in (i) or the components defined in (ii) in the absence of a solvent and in the presence of a lipase such that the molar ratio of acid groups to hydroxyl groups in the reactants is 1:.1 to 1:1.1.

As used herein the term "polyester" is intended to encompass materials produced by the process of the invention from any suitable combination of the monomers defined herein.

The process may be considered as proceeding in two steps. The first step is the oligomerisation step which is complete when substantially all the initial monomers have reacted to form oligomers. The second step may be considered as the conversion of the resulting oligomers to a polyester.

Aliphatic hydroxycarboxylic acids suitable for use in the process of the present invention include those of formula:

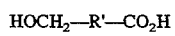

$$HOCH_2—R'—CO_2H$$

wherein $R'$ is a bond or a divalent radical of a substituted or unsubstituted $C_1$ to $C_{12}$ alkyl group optionally having one or more carbon-carbon double bonds and optionally having one or more carbon-carbon triple bonds.

Suitable aliphatic dicarboxylic acids include those of formula:

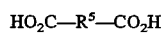

$$HO_2C—R^5—CO_2H$$

wherein $R^5$ is a bond or is a divalent radical defined as for $R'$.

Suitable aliphatic diols include those of formula:

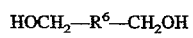

$$HOCH_2—R^6—CH_2OH$$

wherein $R^6$ may be a bond or is a divalent radical defined as for $R'$.

Suitable aliphatic polyols include those of formula:

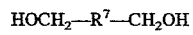

$$HOCH_2—R^7—CH_2OH$$

wherein $R^7$ is a divalent radical defined as for $R'$ and bearing at least one hydroxyl substituent.

Suitable aliphatic hydroxyamines are of formula:

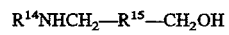

$$R^{14}NHCH_2—R^{15}—CH_2OH$$

where $R^{15}$ is a bond or is a divalent radical defined as for $R'$ and $R^{14}$ is hydrogen or a $C_1$ to $C_{12}$ alkyl group.

Each of the $C_1$ to $C_{12}$ alkyl groups mentioned above may be substituted or unsubstituted and may be cyclic, branched or straight chain, optionally having at least one carbon-carbon double bond, either in the cis- or trans-conformation and optionally having at least one carbon-carbon triple bond. When the $C_1$ to $C_{12}$ alkyl group has more than one double or triple carbon-carbon bond, these bonds may be conjugated or non-conjugated. The $C_1$ to $C_{12}$ alkyl group is optionally substituted with one or more substituents (which, when there are two or more substituents, may be the same or different) each selected from halogen atoms, for example, fluorine, chlorine or bromine, hydroxyl, —$NHR^2$ where $R^2$ is hydrogen or a $C_1$ to $C_{12}$ alkyl, —$OR^3$ where $R^3$ is hydrogen or a $C_1$ to $C_{12}$ alkyl, carboxyl, and —$CO_2R^4$ where $R^4$ is hydrogen or a $C_1$ to $C_{12}$ alkyl.

Preferably the diol has from 2 to 14 carbon atoms and is an α,ω-diol, for example 1,4-butanediol, diethylene glycol, ethylene glycol, propylene glycol, pentanediol, hexane-1,6-diol or dodecane -1,12 diol, most preferably 1,4-butanediol.

Preferably the hydroxyamine is diethanolamine. Preferably the diacid has from 2 to 14 carbon atoms, for example, oxalic acid, succinic acid, fumaric acid, citric acid, malic acid, malonic acid, maleic acid or adipic acid. Most preferably it is adipic acid.

Preferably the hydroxycarboxylic acid has from 2 to 14 carbon atoms, for example glycolic acid, lactic acid, 2-hydroxybutyric acid, 2-hydroxy isobutyric acid, 2-hydroxy caproic acid, 2-hydroxy isocaproic acid, citric acid or malic acid.

As used herein the term "carboxylic acid derivative" refers to esters and acid anhydrides. An ester of a diacid may be a monoester or a diester, for example a mono or dialkyl ester. Preferably the alkyl groups are each of 1 to 4 carbon atoms, and more preferably the derivative is a methyl or ethyl ester or diester, most preferably methyl adipate or dimethyl adipate.

Diethylene glycol has a lower activity than other suitable diols so that, when diethylene glycol is used as monomer, it is necessary to carry out the reaction either at higher temperature, in which case the dispersity is relatively wide, or at low temperature for a long period.

The polyol has at least three hydroxyl groups of which at least two must be non-sterically hindered primary or secondary hydroxyl groups. Preferably the polyol has 3, 4 or 5 hydroxy groups. Tertiary hydroxyl and sterically hindered primary and secondary hydroxyls are unlikely to react under the conditions of the present invention but will nevertheless provide branch points when subsequently reacted with isocyanates. Suitable polyols include pentaerythritol and triols, especially glycerol. Use of glycerol generally results in a linear polymer as the enzyme preferentially esterifies the primary hydroxyls, the secondary hydroxyl being sterically hindered, but branched products may be obtained using certain enzymes.

The polyesters of the present invention may be linear or branched. Branched polymers and linear polymers having pendant hydroxyl or amino groups are generally formed by introducing a small percentage of a branched polyfunctional monomer such as trimethylopropane (TMP), dimethylolpropanoic acid (DMPA), pentaerythritol (PE) or glycerol. Incorporation of such monomers gives rise to both linear and branched polyesters. The resulting linear polyesters generally have pendant hydroxyl groups which lead to branching/cross linking if the polyester is converted into a polyurethane by quenching with isocyanate.

Similarly, hydroxy acids must have a non-sterically hindered primary or secondary hydroxyl. Preferred hydroxy acids are hydroxy-straight chain aliphatic carboxylic acids. The preferences expressed above in relation to primary and secondary hydroxyl groups apply equally to the amino groups present in the hydroxyamines, aminocarboxylic acids, diamines and polyamines.

At high dilution certain hydroxy carboxylic acids tend to form lactones and it is therefore preferred that, when such hydroxy acids are used in the present process, they are used only in high concentration in order to avoid the unwanted lactonisation reaction.

Owing to the low temperatures used in the present process compared with those of conventional chemically catalysed polyesterifications, it is possible to use diacids and hydroxyacids, such as oxalic acid, lactic acid and glycolic acid, which decarboxylate at elevated temperatures and it is thereby possible to produce polyesters not generally accessible by previous methods.

In one embodiment the polyesters produced by the present process may consist of repeating units of one or more hydroxyacids.

In alternative embodiments the polyesters produced by the present process may comprise or consist of repeating units of a diacid and a diol; a diacid and a polyol; a diacid, a diol and a polyol; a diacid, a diol and a hydroxy acid; a diacid, a polyol and a hydroxy acid; a diacid, a diol, a polyol and a hydroxy acid; a diacid, a diol and a hydroxyamine, or any other suitable combination of monomers, for example combinations in which the diacid is replaced by its methylester or ethyl ester derivative. Preferred combinations of monomers are adipic acid/butanediol/ethanolamine, dimethyladipate/1,4-butanediol, adipic acid/methylethanolamine, ethanolamine/adipic acid, diethanolamine/adipic acid, ethanolamine/dimethyladipate, N-methylethanolamine/dimethyladipate, diethanolamine/dimethyl adipate, adipic acid/glycerol, adipic acid/1,4-butanediol, adipic acid/diethylene glycol, adipic acid/diethylene glycol/glycerol, adipic acid/diethylene glycol/trimethylolpropane, diethylene glycol/adipic acid/dimethylolpropane, adipic acid/1,6-hexanediol.

The reactive carboxylic acid groups and reactive hydroxy groups of the reactants are generally present in substantially equal numbers. The reaction may be carried out with a stoichiometric imbalance, but this generally results in a product having a lower weight average molecular weight than if the reactants are used in equimolar amounts. However, in particular aspects of the invention, the proportions may be adjusted slightly such that a polyester having terminal acid units or terminal hydroxy units is obtained. Polyesters having terminal acid units are useful in a variety of coating compositions whereas those with terminal hydroxy units may be used as the soft segments in production of polyurethanes. In particular it is preferred that the molar ratio of acid groups to hydroxyl groups is from 1:1 to 1:1.1 such that a hydroxyl-terminated product is obtained.

In the case where the resulting polymer has terminal hydroxy groups the length of the polymer may be varied by varying the excess of hydroxyl groups present in the initial reaction mixture. For example, increasing the amount of hydroxyl groups relative to the number of acid groups in the reaction mixture will give rise to polymers of shorter chain length.

The enzyme used in the process of the present invention may be bound on an inert carrier, for instance a polymer such as an anion exchange resin, an acrylic resin or a polypropylene, polyester or polyurethane resin or may be used in free form. When the enzyme is bound on an inert carrier it can easily be removed from the reaction mixture (e.g. by filtration) without the need for complicated purification steps. Preferably the enzyme is recovered from the reaction mixture and re-used. Preferably the enzyme is present in isolated form.

The enzyme may be present in the reaction vessel until the reaction reaches completion. Alternatively, the enzyme may be removed from the reaction vessel after the initial oligomerisation step of the reaction has reached completion; in the case where hydroxyl groups are present in excess, the initial step is complete when all the carboxylic acid bearing monomers have reacted to form an acid/base adduct. The enzyme may be removed after completion of the first step of the reaction for example by filtration.

When the enzyme is removed immediately after completion of the initial oligomerisation, the further step of converting the resulting oligomers into a polyester must be carried out with removal of water, or other condensation products (e.g. methanol or ethanol when methyl or ethyl esters of carboxylic acids are used as monomers) which then drives the reaction to form products.

Removal of the enzyme after the initial oligomerisation step is advantageous to avoid damage to the enzyme during the conversion to polyester or polyester(amide). As the reaction proceeds, the viscosity of the reactants increases and the increased shearing forces needed to stir the reaction mixture may cause damage to the enzyme. In addition, the conversion of oligomers to polyester may be accelerated by raising the reaction temperature to at least 80° C., for example at least 85° C., 90° C., 95° C. or 100° C. These high temperatures may cause the enzyme to denature, generally irreversibly. It is therefore advantageous to remove the enzyme from the reaction mixture after the initial oligomerisation is complete.

Surprisingly, when the enzyme is removed after completion of the initial oligomerisation the reaction may be driven by the removal of water (or other condensation product) and it is not necessary to adopt the severe conditions used in the prior art.

Suitable enzymes are commercially available lipases. Not all lipases function as polyesterification catalysts in the presence of substantial quantities of water (an example is the lipase from *Mucor meihei*) so it may be necessary either to remove water during the reaction to retain the activity of the enzyme or to select enzymes which function when water is present.

Surprisingly it has been found that many of the enzymes used in the reaction of the present invention are still active in the presence of water. Therefore removal of water is only necessary when the enzyme has been removed from the reaction mixture, generally after completion of the initial oligomerisation. In those cases when enzyme is left in the reaction throughout, removal of water, whilst not strictly necessary, is usually preferred.

A preferred enzyme for use in the present process is the lipase derived from *Candida antarctica*, a non-specific triacylglycerol lipase [E.C. no.3.1.1.3] for instance that available from Novo Industri AS, Novozym 435* where the enzyme is immobilised on a macroporous acrylic resin. This enzyme may be obtained commercially by recombinant DNA techniques having the native sequence or genetically engineered modifications thereof although it may be extracted from the organism if desired. Other suitable lipase can be identified by simple trial-and-error experimentation within the ability of those skilled in the art.

*Novozym 435 is a registered Trade Mark

The activity of the enzyme may be affected by materials present in the reaction mixture, for example the lipase from *C. antarctica* is inhibited by glycerol. It is preferable not to include branched polyfunctional monomers, particularly secondary alcohols, in the initial reaction mixture, but to delay their addition until after the reaction is started to avoid reducing enzyme activity. Preferably branched polyfunctional monomers are not added to the reaction mixture until after the enzyme has been removed, for example after completion of the initial oligomerisation step. If a branched polyfunctional monomer is added to the reaction mixture at least 12 hours, for example at least 14 hours, 16 hours or 24 hours after the start of the reaction, when the enzyme is still present in the reaction mixture the enzyme activity will be reduced, but not completely, and the reaction will continue at a slower rate than if the branched polyfunctional monomer had not been added.

The amount of enzyme used is not critical and is generally limited by economic considerations. To little enzyme will result in a slow reaction whereas too much enzyme simply increases the costs unnecessarily. With the lipase from *Candida antarctica* (Novo Industri AS Catalogue no SP 435) it has been found convenient to use from 0.1 to 1.5% by weight of supported enzyme based on the total weight of monomers, preferably 0.1 to 0.6% and most preferably 0.15 to 0.3% of enzyme.

Both stages of the process are generally carried out at from 10° C. to 90° C., preferably 40° to 60° C. Above 90° C., most enzymes will denature but enzymes may be used which have a denaturation temperature higher than 90° C. and the steps of the reaction when the enzyme is present may then be carried out above 90° C. Below 10° C. the reaction is very slow and the reaction takes an uneconomically long time to go to complete conversion of the monomers. When the enzyme is removed after the oligmerisation step, the conversion of oligomers to polymer is generally carried out at temperatures of from 10° C. to 90° C., preferably 40° C. to 80° C., although the reaction may be accelerated by raising the temperature above 90° C.

Whilst it is preferred for most applications to work at elevated temperatures such as 40° to 60° C. to reduce the duration of reaction, where a particularly narrow dispersity is required, low temperatures and long reaction times may be used.

The process is generally carried out at atmospheric pressure or reduced pressure. The water produced by the reaction is generally removed during or after the reaction, for example after the initial oligomerization and during the subsequent conversion of oligomers to polyesters. The water is conveniently removed by reducing the pressure under which the reaction is carried out, for example to 100mbar or 50 mbar, preferably to 5 mbar. Alternatively the water may be removed with a wiped film evaporator under reduced pressure, for instance, 5 mmHg or even 1 mm Hg (1 mmHg=133.322 Pa) or less. In another alternative method a desiccant such as a molecular sieve is used, taking precautions to avoid physical damage to supported enzymes due to abrasion between the desiccant and the enzyme support.

Generally, the process is carried out in the presence of enough water to hydrate the enzyme and substantial quantities of water may be present without affecting the polyesterification. However removal of most of the water (i.e. apart from that required to hydrate the enzyme) will be required at least at the end of the reaction if complete conversion to polyester is to be achieved.

The requirements for the reaction mixture apply equally to the removal of alcohol, such as methanol or ethanol, produced by the reaction in which monomers bearing carboxylic acid ester groups are used.

It has been discovered that the presence of water at the start of the reaction unexpectedly increases the rate of reaction.

The total reaction time is generally from 6 to 48 hours, preferably from 12 to 24 hours.

The enzyme is generally removed from the reaction mixture at between 1 and 24 hours after the reaction is started, for example, 2, 4, 12, 18 or 24 hours after the reaction is started. Typically the reaction is continued for at least 10 hours, for example 12, 14, 18 or 24 hours after removal of the enzyme.

The process of the present invention generally enables the production of high weight average molecular weight polyesters and polyester(amide)s, for instance up to or higher than 8 kDa, especially up to or higher than 10 kDa.

The polyesters and polyester(amide)s produced by the process of the present invention generally have a minimum weight average molecular weight of 200 Da, preferably 600 Da, more preferably 1000 Da and most preferably 4 kDa. The weight average molecular weight of the polyester or polyester(amide) is measured using gel permeation chromatography.

The polyesters and polyester(amide)s produced by the process of the present invention generally comprise from 6 to 50 monomer units, preferably from 10 to 40 monomer-units and most preferably from 30 to 40 monomer units. Generally it has an acid number of from 0 to 50, preferably from 0 to 25 and more preferably from 0.5 to 10. Most preferably the polyester or polyester(amide) has an acid number of about 1.

The polyesters and polyester(amide)s produced by the process of the invention generally have a dispersity of 1.5 or less, preferably 1.3 or less. The dispersity is calculated as follows:

$$\text{Dispersity}, d = \frac{\text{Weight Average Molecular Weight}}{\text{Number Average Molecular Weight}}$$

and the number and weight average molecular weights may be obtained by suitable methods.

The polyesters produced by conventional processes generally contain at least 0.5% or more, for instance up to 1.5% or more by weight of cyclic diester impurities such as the cyclic ester 1,6-dioxacyclododecane-7,12-dione. When necessary, the cyclic diester impurity content is reduced by methods such as wiped film evaporation or high vacuum distillation. After distillation, contents of from as low as 0.3 to 0.7% by weight of the cyclic diester impurities can be achieved. This level of impurity is often acceptable but is achieved at great expense. The presence of cyclic diester impurities is detected using gas chromatography mass spectrometry or High Performance Liquid Chromatography (HPLC).

The process of the present invention is carried out in the absence of solvent. According to the present invention a solvent is an organic liquid which is inert under the reaction conditions of the present invention.

One of the problems of using adipic acid in solventless polyesterification reactions is that adipic acid is only sparingly soluble in the other monomers such as a diol or polyol. In the process of the present invention low molecular weight oligomers and dimers are the initial reaction products. Adipic acid dissolves in the low molecular weight products and the reaction then accelerates to produce higher molecular weight polymers.

According to a preferred embodiment of the present invention the polyesters having hydroxy terminal groups are further reacted with at least one isocyanate to produce polyurethanes. Generally the enzyme is removed from the polyester before the reaction with isocyanate. This prevents the enzyme and its support from interfering with the polyester/isocyanate reaction. Generally water produced during the polyesterification is removed before reaction with isocyanate.

The polyesters of the invention have sharp melting points (unlike previously produced materials with wide dispersity) and impart to the polyurethanes excellent physical properties such as desirable combinations of hardness and flexural and tensile strength.

Certain polyesters produced in accordance with the present invention are novel materials and form further aspects of the invention.

In one aspect the present invention provides a polyester having a dispersity of 1.5 or less, especially such polymers comprising residues of at least one aliphatic dicarboxylic acid and at least one aliphatic diol as repeating units.

In a further aspect of the invention there is provided a polyester comprising as repeating units the residues of at least one of oxalic acid, lactic acid and glycolic acid.

Preferences expressed above in relation to the compositions of the polyesters apply to these two aspects of the invention as well.

The polyesters and polyurethanes of the present invention find uses as shaped articles and foams, particularly for motor vehicles.

The invention will now be illustrated by the following Examples which are not intended to limit the scope of protection.

EXAMPLE 1

Materials

1. Adipic acid, Aldrich 9.83 g, 0.066 mole, 1 eq.
2. Glycerol, Fison's 6.30 g, 0.070 mole, 1.05 eq.
3. Lipase SP 435, BX LC 002, 91/7, Novo, 200 mg.

Procedure

The reagents were charged to a test-tube type, 80 ml cell reactor (CR) to which a rugby ball magnetic stirrer was added. The CR was heated in an oil bath at 40° C. and the contents were stirred magnetically once the viscosity had dropped. Stirring was carried out for 5 hours in the open vessel, and then the CR was fitted with a T-piece adaptor, in the top of which was fitted a purging tap. Vacuum (10 mbar, falling to 5 mbar) was applied via the side arm for a further 5 hour period. Though there was a proportion of unreacted adipic acid, GPC measurement showed clearly an oligomeric mix.

Analytical Techniques

The course of the polycondensation reaction can be monitored qualitatively by thin layer chromatography, as there is an approximate correlation between retention factor and molecular size. The most suitable eluant for the adipic acid/1,4-butanediol system is a 10:1 (volume) mixture of dichloromethane and ethanol, with which the diol appears at $R_f 0.18$ and the ester products in the range $R_f 0.26–0.70$, progressively higher with chain growth although resolution is not sufficient to allow identification of individual oligomers. The diol and products stain blue when visualised with p-anisaldehyde and heat.

The presence of lower ester products in the reaction residues, most notably the three- and five-component hydroxy terminated oligomers, was confirmed through multistage column chromatography. Despite the chemical similarity and mutual solubility of the oligomers, which make complete separation difficult to achieve, product fractions containing one dominant species can be obtained, allowing identification by conventional spectroscopic means. Cross-referencing of the chromatographic data from each fraction then gives the retention factors of each component, from which their present in or absence from subsequent reaction residues can readily be assessed.

The lower weight product fractions were characterised by infrared and proton NMR spectroscopy, mass spectrometry and gel permeation chromatography. IR can give little indication of chain length other than some variation in the relative intensity of the hydroxyl absorption), but will clearly show the significant end groups. The most important diagnostic features are, for hydroxyl, a strong absorption around 3450 cm$^{-1}$(O-H stretch); for carboxyl, a very broad absorption in the range 2400–3600 cm$^{-1}$(O-H stretch) and a broadening of the carbonyl (C=O stretch) absorption to below 1720 cm$^{-1}$.

Proton NMR not only provides confirmation of the oligomer end groups, but can also be used to estimate the number of repeat units. The signals found in this system are a multiplet at 1.66–1.68 ppm (central, or b, methylenes), a labile singlet at 1.70–2.10.ppm (hydroxyl), a multiplet at 2.33–2.34 ppm (methylene adjacent to carbonyl), a triplet at 3.66–3.70 ppm (methylene adjacent to hydroxyl), a triplet at 4.10–4.14 ppm (methylene adjacent to ester oxygen) and a broad and labile singlet at 7.00 ppm (combined hydroxyl and carboxyl). The chain length may be determined from the relative intensity of an end group signal. In a free acid residue, the hydroxyl singlet is often concealed within the chain methylene multipier and the carboxyl singlet, if seen, is liable to exaggeration because of hydrogen bonding to traces of water, so the most reliable signal for use as a scaling factor is the CH$_2$OH triplet at around 3.68 ppm. With all-hydroxy termination, for example, this must have a proton number of four, so the sum of the integrations can be translated into the total hydrogen content of the molecule, which equals 26+16 n where n is the number of repeat units (or, in the case of a mixture of similar oligomers, the number average degree of polymerisation). This technique is useful for low oligomers of four units or fewer; with longer chains the inaccuracy in the integrations usually leads to an uncertainty in n greater than one.

Unambiguous confirmation of oligomer identity is provided by mass spectrometry. Using chemical ionisation by ammonia bombardment, molecular ions are found in combination with hydrogen and ammonium, that is, at M+1 and M+18, up to a molecular weight of 600–700 Daltons, above which the chains tend to fragment.

The principal technique used for analysis of the polycondensation residues was gel permeation chromatography. The sample is dissolved in tetrahydrofuran and the solution passed through a column packed with a polymer gel. Components are separated according to their molecular volume, the smaller substances tending to divert into the pores and thus follow a longer route than large molecules which pass directly through the interstices. The solution of the various components is monitored by a differential refractometer and a plot produced of intensity against retention time, expressed as distance on the chart paper. The relationship of retention factor to molecular size is logarithmic, hence substances in the lower size range are very well resolved and give rise to peaks which can be individually identified, whilst resolution decreases with greater size and signals eventually coalesce at a point determined by the maximum pore dimension of the column. Where the constituents of the sample are structurally similar, molecular weight can be regarded as proportional to molecular volume for practical purposes.

Above the region where oligomers can be individually characterised, the condensation products have been classified into molecular weight ranges by comparison of the retention factors of the measured elution peaks with those of polyethylene glycol reference standards. The data on which analysis of the residues is based are as follows:

| Species | Retention factor/cm (±0.1) | | Molecular mass/Daltons |
|---|---|---|---|
| | 50Å Column | 500Å Column | |
| Tetrahydrofuran | 16.5 | 18.9 | 72 |
| Diethylene glycol | 16.0 | | 106 |
| 1,4-butanediol (B) | 15.7 | 18.2 | 90 |
| Adipic acid (A) | 14.5 | 17.6 | 146 |
| AB | 14.0 | 17.2 | 218 |
| BAB | 13.6 | 16.8 | 290 |
| PEG 440 | 13.3 | | 440 |
| B(AB)$_2$ | 12.6 | | 490 |
| PEG 600 | 12.6 | | 600 |
| B(AB)$_3$ | 12.2 | | 690 |
| PEG 960 | 12.0 | | 960 |
| PEG 1450 | 11.6 | | 1450 |
| PEG 4250 | | 13.04 | 250 |
| PEG 7100 | | 12.17 | 100 |

Gel permeation chromatography was performed by Baxenden Chemicals Ltd. using Waters 440 series chromatographic equipment with THF as the mobile phase. The columns, manufactured by Polymer Laboratories Ltd., were of dimensions 600×7.5 mm and packed with PL gel, a highly crosslinked spherical polystyrene/divinylbenzene material of particle size 10 µm and pore size 50 Å (or 500 Å where specified). The detector was a Waters model 401 differential refractometer, and estimates of molecular weight average were made by a BBC model B microcomputer from a calibration against commercial PEG samples.

Estimates of the number average and weight average molecular weights, $M_n$ and $M_w$, of the product mixtures are computer-generated by calibration against commercial PEG standards and have been corrected to the known mass of residual starting material (in most cases, adipic acid, MW 146). These figures are calculated from approximate relationships and thus have lower intrinsic accuracy than direct comparisons of retention, but nonetheless they provide a convenient measure of experimental results. The confidence band of the corrected averages is estimated at ±10%.

EXAMPLE 2

Materials

1. Adipic acid (AA), Aldrich, 196.6 g, 1.35 mole 1 eq.

2. 1,4-Butanediol (BD), Aldrich, 127.3 g, 1.41 mole 1.05 eq.

3. Lipase SP 435, BX LC 002, 91/7, Novo, 1 g (0.15% by weight of monomers).

Procedure

The adipic acid, butanediol and lipase were charged to a 500 ml flange flask and the flask heated in an oil bath at 40° C. The viscous mix was stirred with a wooden spatula, then left in the oil bath for 0.5 hour till a mobile sludge was generated. The flange flask was then fitted with a rugby ball stirrer (4 cm) and a 5 neck vessel lid fitted with a vacuum take off and a purging tap. Waterpump vacuum was applied for 22 hours whilst the mix was slowly stirred to avoid abrading the enzyme. After 2 hours the mixture formed a clear mobile solution with only the immobilized enzyme insoluble. High vacuum was applied via a rotary oil pump and the vacuum dropped from 10 mbar to 5 mbar over 3 hours. Purging was continued for a total of 5 hours. The finished product either set solid towards the end of the reaction or subsequently on standing.

Wt. 250 g approx.
Acid. No. 6
Hydroxyl No. 35

| Molecular weight | |
| --- | --- |
| Number average Mn | 5020 |
| Weight average Mw | 7466 |
| Dispersity | 1.49 |
| Butane diol content | <0.01% |
| Water content | 0.18% |
| Cyclic ester content | <0.1% |

Materials

1. Adipic acid (AA), Aldrich, 590 g, 4.04 mole, 1 eq.

2. 1,4-Butanediol (BD), Aldrich, 382 g, 4.24 mole, 1.05 eq.

3. Lipase SP 435, BX LC 002, 91/7, Novo, 3 g (0.15% by weight of monomers).

Procedure

The adipic acid, butanediol and lipase were charged to a 1 liter flange flask and the flask heated in an oil bath at 40° C. The viscous mix was stirred with a wooden spatula, then left in the oil bath for 0.5 hour till a mobile sludge was generated. The flange flask was then fitted with an overhead stirrer and a 5 neck vessel lid fitted with a vacuum take off and a purging tap. Water pump vacuum was applied for 22 hours whilst the mix was slowly stirred to avoid abrading the enzyme. After 2 hours the mixture formed a clear mobile solution with only the immobilized enzyme insoluble. High vacuum was applied via a rotary oil pump and the vacuum dropped from 10 mbar to 5 =bar over 3 hours. The oil bath temperature was raised to 60° C. and purging was continued for a total of 17 hours. The finished product either set solid towards the end of the reaction or subsequently on standing. The product was freed from the enzyme catalyst by filtration through polypropylene fine mesh.

| Wt. | 650 g |
| --- | --- |
| Acid No. | 8 |
| Hydroxyl No. | 36 |
| Molecular weight | |
| Number average Mn | 4783 |
| Weight average Mw | 7139 |
| Dispersity | 1.49 |
| Butane diol content | 0.21% |
| Water content | 0.08% |
| Cyclic ester content | 0.12% |

EXAMPLE 4

Materials

1. Adipic acid, Aldrich, 196.6 g, 1.35 mole, 1 equiv.

2. Diethylene glycol, Chemi Trade, 160.2 g, 1.51 mole, 1.12 equiv.

3. Lipase, Novozym 435, 1.03 g (0.29%

4. Water 6.8 ml (1.9%

Process

The diethyleneglycol (DEG)/water was charged to a 500 ml flask. The flask wad heated in an oil bath at 40° C. An overhead stirrer/flange lid was fitted. When the flask contents had reached 40° the adipic acid was added with rapid stirring. The stirring speed was reduced and the enzyme was added. The slurry was stirred at 40° for 6 hours and then at 60° for a further 19 hour period. Acid number monitoring showed a value of 141 and the flask contents were a mobile liquid. Vacuum was applied (100 mbar) for 1.5 hr and the enzyme was filtered off via a 74 micron nylon cloth directly into a second flask. Stirring speed was set at an increased rate and the oligomer subjected to vacuum strip at 80° C. initially 20 mbar then 10 mbar reducing to 5 mbar).

| MATERIAL CHARACTERISTICS | |
| --- | --- |
| Bx Size - Kg: | 350 g |
| OH No - : | 54.4 |
| Acid No - : | 5.3 |
| Molecular wt: | 2063 |
| $M_n$ - GPC: | 2233 |
| $M_w$ - GPC: | 4493 |
| Dispersity: | 2.01 |
| Water content: | 0.0537 |
| Cyclic Ester content: | 1.5% |

EXAMPLE 5

Incorporation of Branched Polyfunctional Monomer

| MATERIALS |
| --- |
| 1. Diethylene glycol (DEG), FW 106, 617.4 g, 5.82 mole, 1.08 eq. |
| 2. Water 27.2 g (1.9% w/w DEG + AA) |
| 3. Adipic acid (AA), ex ICI, FW 146, 786.4 g, 5.39 mole, 1.0 eq. |
| 4. Lipase, Novozym® 435, Bx 0013-1, 92-6, 4.12 g (0.29% w/w DEG + AA) |
| 5. Glycerol, ex Fison's, FW92, 0.1628 mole, 0.0302 eq, 2.43% w/w DEG, 1.074 w/w DEG + AA. |

Process

DEG and water was charged to a two liter flange flask equipped with an overhead stirrer and lid. The temperature of the flask contents was controlled by a metal probe linked to an isomantle. The flask contents were heated to 40° C. and adipic acid added with rapid stirring. The stirring speed was reduced and the enzyme added. The resulting slurry was stirred at 40° C. for 6 hrs and then at 60° for a further 19 hours. Acid number monitoring showed a value of 129. The flask content was a mobile liquid. The flask contents were filtered through a 74 micron nylon cloth to remove the enzyme. Glycerol was added to the resulting clear liquid and the oligomer subjected to vacuum strip (initially at 20 mbar, finally at 5m bar) with the temperature initially at 60° and finally at 80° with increased agitation. Depletion of free glycerol content was determined by G.C. assay.

The characteristics of the resulting material are as show in Table 1.

EXAMPLE 6

Replacement of Glycerol with Trimethylolpropane

MATERIALS

1. Diethylene glycol, FW106, 154.4 g, 1.46 mole, 1.08 eq.
2. Water 6.8 mls. (1.9% w/w DEG + AA).
3. Adipic acid, ex ICI, FW 146, 196.6 g, 1.35 mole, 1.0 eq.
4. Lipase, Novozym® 435, BX 0013-1, 92-6, 1.03 g, 0.29% w/w (DEG + AA).
5. Trimethylolpropane (TMP), ex Aldrich, FW 134, 5.49 g, 0.041 mole, 0.030 eq, 3.6% w/w DEG, 1.6% w/w (DEG + AA)

Process

The process was carried out as in Example 5 with the exception that oil bath heating replaces isomantle heating. Trimethylolpropane is added after the enzyme has been filtered off, prior to the final vacuum water strip. Depletion of free TMP was monitored by gas chromatography (GC).

The resulting material had the characteristics as shown in Table 1.

EXAMPLE 7

Replacement of TMP by Dimethylolpropionic Acid (DMPA)

Materials

1. Diethylene glycol, FW 106, 156.1 g, 1.47 mole, 1.104 eq.
2. Water, 6.8 mls (1.9% w/w DEG+AA).
3. Adipic acid, ex ICI, FW 146, 194.8 g, 1.33 mole, 1 eq.
4. Lipase, Novozym® 435, Bx 0013-1, 92-6, 1.03 g (0.29% w/w DEG+AA)
5. Dimethylolpropane, ex Aldrich, FW 134, 3.19 g, 0.024 eq. 2% w/w DEG 0.91 % w/w (DEG+AA).

Process

The reaction was carried out in the same was as for Example 6, but with TMP replaced by DMPA. Incorporation of DMPA into the polymer matrix was evidenced by depletion of free DMPA, measured using ion-pair Reverse Phase Liquid Chromatography.

Characteristics of the resulting material are shown in Table 1.

EXAMPLE 8

Production of Polyester/Polyamide

Materials

1. Dimethyl adipate, FW 174, 11.48 g, 0.066 mol, 1 eq.
2. N-Methylethanolamine, Aldrich, FW 75, 5.20 g, 0.0693 mol, 1.05 eq.
3. Lipase, Novozym 435, BX 0013-1, 92-6, 200 mg. (1.2% w/w combined substrate).

Process

The liquid components were charged to a cell reactor and warmed to 50° with magnetic stirring for 18 hrs after adding the lipase. Monitoring by G.C. showed 100% uptake of dimethyladipate.

GPC monitoring showed a set of short chain oligomers, viz dimer to 8-mer species with $M_w$ 405, $M_n$ 327 and poly dispersity index 1.24. Subsequently, application of a high vacuum, 5–10 mbar, to the cell reactor, at bath temperature 60° for 18 hrs led to an oligomeric mix. Characterisation by GPC showed that the mixture was significantly higher in degree of polymerization viz $M_w$ 762, M 546, dispersity 1.4. The observed changes point to a "living" polymerization process in which the mono adduct "acid/base" (AB) is acting as the progressive unit.

The characteristics of the resulting material are shown in Table 1.

TABLE 1

|  | EXAMPLE 5 | EXAMPLE 6 | EXAMPLE 7 | EXAMPLE 8 |
| --- | --- | --- | --- | --- |
| Acid No. | 3.04 | 4.75 | 9.12 | N/R |
| OH No. | 59.49 | 63.35 | 58.26 | N/R |
| Molecular Wt. | 1886 | 1717 | 1926 | N/R |
| $M_n$ - GPC | 2253 | 2462 | 2045 | 546 |
| $M_w$ - GPC | 4965 | 4808 | 4300 | 762 |
| Dispersity | 2.20 | 1.95 | 2.10 | 1.4 |
| Water Content (%) | 0.027 | 0.035 | 0.029 | N/R |
| Cyclic Ester Content (%) | N/R | N/R | N/R | N/R |
| Viscosity (cps) | 490 | 8680 | 75°:485 100°:210 | N/R |
| Free Monomer Content (%) | <0.1 ± 0.02 | <0.1 | 0.3 ± 0.05 | 0.9 |

Preliminary experiments were carried out to determine the feasibility of various polymerisation reactions. The results are shown in Table II.

TABLE II

TABLE OF FINDINGS - AA/DMA EA/NMEA/DEMA

| SUBSTRATE A | SUBSTRATE B | POLYMERIZATION YES/NO |
| --- | --- | --- |
| AA | EA | YES |
| DMA | EA | YES |
|  | NMEA | YES |
|  | DMEA | YES |

AA = adipic acid

TABLE II-continued

TABLE OF FINDINGS - AA/DMA EA/NMEA/DEMA

| SUBSTRATE A | SUBSTRATE B | POLYMERIZATION YES/NO |
|---|---|---|

DMA = dimethyladipate
EA = ethanolamine
NMEA = N-methylethanolamine
DMEA = dimethylethanolamine

We claim:

1. A process for producing a polyester comprising as repeating units
    (i) residues of at least one aliphatic hydroxycarboxylic acid monomer selected from the group consisting of aliphatic hydroxycarboxylic acids and esters and anhydrides thereof or
    (ii) residues of (a) at least one aliphatic dicarboxylic acid monomer selected from the group consisting of aliphatic dicarboxylic acids and esters and anhydrides thereof, (b) at least one aliphatic hydroxyamine, diol or polyol, and optionally (c) at least aliphatic hydroxycarboxylic acid monomer selected from the group consisting of aliphatic hydroxycarboxylic acids and esters and anhydrides thereof;
    which process comprises reacting the components defined in (i) or components defined in (ii) in the absence of a solvent and in the presence of a lipase, the molar ratio of acid groups to hydroxyl groups in the reactants being 1:1 to 1:1.1.

2. A process according to claim 1 wherein the dicarboxylic acid monomer has from 2 to 14 carbon atoms in the dicarboxylic acid moiety.

3. A process according to claim 1 wherein the dicarboxylic acid monomer is adipic acid.

4. A process according to claim 1 wherein the dicarboxylic acid ester is a methyl or ethyl diester.

5. A process according to claim 1 wherein the diol has from 2 to 14 carbon atoms.

6. A process according to claim 1 wherein the diol is 1,4 butanediol, 1,6 hexanediol or diethylene glycol.

7. A process according to claim 1 wherein the hydroxycarboxylic acid monomer has from 2 to 14 carbon atoms in the hydroxycarboxylic acid moiety.

8. A process according to claim 7 wherein the hydroxyacid is glycolic acid or lactic acid.

9. A process according to claim 1 for producing a polyester consisting of residues of an aliphatic dicarboxylic acid monomer selected from the group consisting of aliphatic dicarboxylic acids and esters and hydrides thereof and an aliphatic diol which process comprises reacting the dicarboxylic acid monomer and the diol in the absence of a solvent and in the presence of a lipase.

10. A process according to claim 1 wherein the polyester has a dispersity of 1.5 or less.

11. A process according to claim 1 wherein the polyester has a dispersity of 1.3 or less.

12. A process according to claim 1 wherein the lipase is from *Candida antarctica*.

13. A process according to claim 1 which further comprises removing the enzyme from the reaction mixture.

14. A process according to claim 13 wherein the enzyme is removed from the reaction mixture when substantially all the carboxylic acid bearing monomers have reacted to form acid/base adducts.

15. A process according to claim 1 wherein the water produced by the reaction is removed from the reaction vessel.

16. A process according to claim 15 wherein the water is removed from the reaction vessel only after the enzyme has been removed.

17. A process according to claim 1 wherein the resulting polyester contains not more than 0.3% by weight of cyclic diester impurities.

18. A process according to any one of the preceding claims wherein the resulting polyester has a weight average molecular weight of 200 to 10,000 Da.

19. A process according to claim 17 wherein the polyester has a weight average molecular weight of 600 to 8000 Da.

20. A process according to claim 1 which further comprises reacting the polyester with isocyanate to form a urethane polymer.

21. A process according to claim 1 which further comprises moulding the polyester or urethane polymer into a shaped article.

22. A process for producing a polyester comprising as repeating units
    (i) residues of at least one aliphatic hydroxycarboxylic acid monomer selected from the group consisting of aliphatic hydroxycarboxylic acids and esters and anhydrides thereof or
    (ii) residues of (a) at least one aliphatic dicarboxylic acid monomer selected from the group consisting of aliphatic dicarboxylic acids and esters and anhydrides thereof, (b) at least one aliphatic hydroxyamine, diol or polyol, and optionally (c) at least aliphatic hydroxycarboxylic acid monomer selected from the group consisting of aliphatic hydroxycarboxylic acids and esters and anhydrides thereof;
    which process comprises reacting the components defined in (i) or components defined in (ii) in the absence of a solvent and in the presence of a lipase, the molar ratio of acid groups to hydroxyl groups in the reactants being 1:1 to 1:1.1, wherein the lipase is removed from the reaction mixture when substantially all the carboxylic acid bearing monomers have reacted to form acid/base adducts.

* * * * *